United States Patent
Schatz et al.

(10) Patent No.: US 6,669,939 B1
(45) Date of Patent: Dec. 30, 2003

(54) (POLY)PEPTIDES WHICH REPRESENT THE EPITOPES OF THE HUMAN HERPES VIRUS TYPE 8

(75) Inventors: Octavian Schatz, Altomunster (DE); Jürgen Haas, Munich (DE)

(73) Assignee: Biotrin International Properties Limited, Mount Merrion (IR)

( * ) Notice: Subject to any disclaimer, the term of this patent is extended or adjusted under 35 U.S.C. 154(b) by 0 days.

(21) Appl. No.: 09/701,432

(22) PCT Filed: May 28, 1999

(86) PCT No.: PCT/EP99/03719

§ 371 (c)(1),
(2), (4) Date: Feb. 8, 2001

(87) PCT Pub. No.: WO99/62938

PCT Pub. Date: Dec. 9, 1999

(30) Foreign Application Priority Data

May 29, 1998 (DE) .......................................... 198 24 244

(51) Int. Cl.[7] .................. A61K 39/15; A61K 39/25; C12P 39/00; C12Q 1/70; G01N 33/68
(52) U.S. Cl. .................. 424/185.1; 424/186.1; 424/192.1; 424/199.1; 424/229.1; 435/4; 435/5; 435/7.1; 435/7.9; 435/69.1; 435/975
(58) Field of Search .................. 424/185.1, 186.1, 424/192.1, 196.1, 199.1, 229.1; 435/4, 5, 7.1, 7.9, 69.1, 975

(56) References Cited

FOREIGN PATENT DOCUMENTS

| EP | 0893504 A1 | * 11/1997 |
|---|---|---|
| EP | 0 893 504 | 1/1999 |
| EP | 0 950 666 | 10/1999 |
| WO | 96/15779 | 5/1996 |
| WO | WO 97/241057 A2 | 7/1997 |
| WO | 97/31932 | 9/1997 |
| WO | 98/04576 | 2/1998 |
| WO | 98/11132 | 3/1998 |

OTHER PUBLICATIONS

Ford et al. protein Expression and Purification 1991, vol. 2, pp. 95–107.*
Lin et al. J. Virol. 1997, vol. 3069–3079.
Michael et al Nature 1981, vol. 294, pp. 563–565.
Tedeschi et al., "Human Serum Antibodies to a Major Defined Epitope Of Human Herpesvirus 8 Small Viral Capsid Antigen", *The Journal of Infectious Diseases*, The Infectious Diseases Society of America, vol. 179:1016–1020, (1999).
Pau et al., "Mapping And Serodiagnostic Application Of a Dominant Epitope Within The Human Herpesvirus 8 ORF 65–Encoded Protein", *Journal of Clinical Microbiology*, American Society for Microbiology, vol. 36(6):1574–1577, (1998).

Davis et al., "Detection of Serum Antibodies To A Kaposi's Sarcoma—Associated Herpesvirus–Specific Peptide", *The Journal of Infectious Diseases*, vol. 175:1071–1079, (1997).
Kaposi, "Idiopathisches Multiples Pigmentsarkom der Haut",. *Arch. Dermatol. Syphil.*
Beral et al., "Kaposi's Sarcoma Among Persons With AIDS: A Sexually Transmitted Infection", *The Lancet*, vol. 335:123–128, (1990).
Archibald et al., "Evidence For a Sexually Transmitted Cofactor For AIDS–Related Kaposi's Sarcoma In A Cohort Of Homosexual Men", *Epidemiology*, Epidemiology Resources Inc., vol. 3(3):203–209, (1992).
Chang et al., "Identification Of Herpesvirus–Like DNA Sequences In AIDS–Associated Kaposi's Sarcoma", *Science*, vol. 266:1865–1869, (1994).
Russo et al., "Nucleotide Sequence Of The Kaposi Sarcoma–Associated Herpesvirus (HHV8)", *Pro. Natl. Acad. Sci. USA*, Microbiiology, vol. 93:14862–14867, (1996).
Huang et al., "Human Herpesvirus–like Nucleic Acid In Various Forms Of Kaposi's Sarcoma", *The Lancet*, vol. 345:759–761, (1995).
Luppi et al., "frequency And distribution of HerpesvirusLike DNA Sequences (KSHV) In Different Stages Of Classic Kaposi's Sarcoma And In Normal Tissues From An Italian Population", *Int. J. Cancer*, Wiley–Liss, Inc., vol. 66:427–431, (1996).
Moore et al., "Detection Of Herpesvirus–Like DNA Sequences In Kaposi's Sarcoma In Patients With and vol. Those Without HIV Infection", *The New England Journal of Medicine*, The Massachusetts Medical Society, 332(18):1181–1191, (1995).
O'Neill et al., "Herpes Virus–like Sequences Are Specifically Found In Kaposi Sarcoma Lesions", *J. Clin Pathol.*, vol. 49:306–308, (1996).
Whitby et al., "Detection Of Kaposi Sarcoma Associated Herpesvirus In Peripheral Blood Of HIV–Infected Individuals And Progression To Kaposi's Sarcoma", *The Lancet*, vol. 346:799–802, (1995).

(List continued on next page.)

*Primary Examiner*—James Housel
*Assistant Examiner*—Bao Qun Li
(74) *Attorney, Agent, or Firm*—Foley & Lardner

(57) ABSTRACT

The present invention relates to (poly)peptides, which are recognized by anti-HHV8 antibodies of HHV-8 infected patients, whereby these (poly)peptides are not naturally occurring HHV-8 proteins. The present invention further relates to polymers, comprising at least two identical or different peptides according to the invention as well as conjugates, comprising said peptides and/or polymers thereof. Furthermore, this invention provides mixtures, comprising said peptides and/or polymers thereof, which are used to detect anti-HHV-8 antibodies with high sensitivity and specificity. In addition, the present invention relates to a diagnostic kit, comprising said peptides, polymers and/or mixtures thereof, which can be used for the detection of anti-HHV-8 antibodies and for the diagnosis of an HHV-8 infection, respectively.

10 Claims, 3 Drawing Sheets

OTHER PUBLICATIONS

Figure 1:
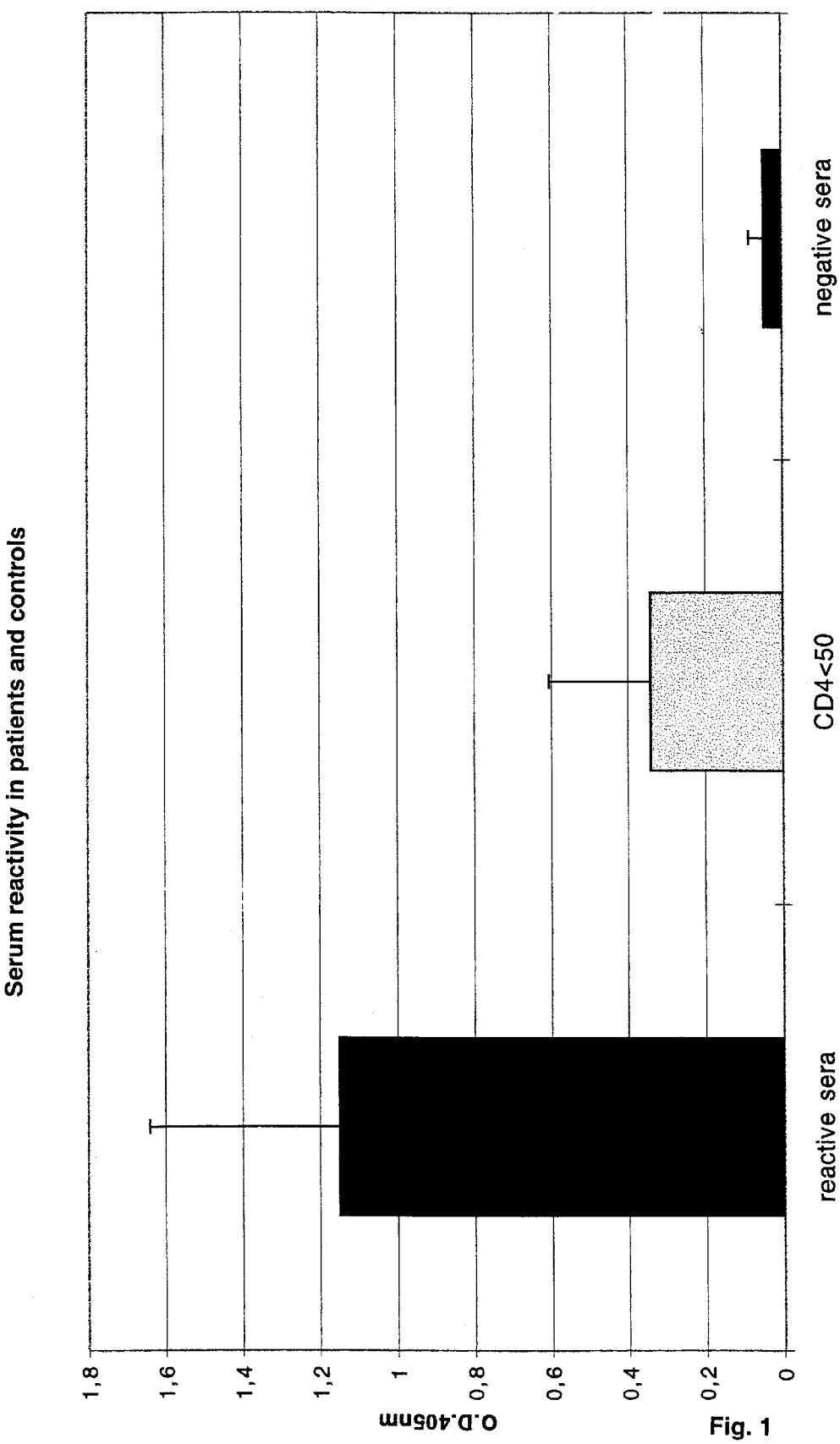

Soulier et al., "Kaposi's Sarcoma–Associated Herpesvirus–Like DNA Sequences In Multicentric Castleman's Disease", *Blood*, vol. 86(4):1276–1280, (1995).

Cesarman et al., "Kaposi's Sarcoma–Associated Herpesvirus–Like DNA Sequences In AIDS–Related Body–Cavity–Based Lymphomas", *The New England Journal Of Medicine*, vol. 332(18):11861191, (1995).

Said et al., "Kaposi's Sarcoma–Associated Herpesvirus/Human Herpesvirus Type 8 Encephalitis In HIV–Positive and –Negative Individuals", *AIDS*, Rapid Science Publishers ISSN 02–9370, vol. 11:1119–1122, (1997).

Rettig et al., "Kaposi's Sarcoma–Associated Herpesvirus Infection Of Bone Marrow Dendritic Cells From Multiple Myeloma Patients", *Science*, vol. 276:1851–1854, (1997).

Lunardi–Iskandar et al., "Tumorigenesis And Metastasis Of Neoplastic Kaposi's Sarcoma Cell Line In Immunodeficient Mice Blocked By A Human Pregnancy Hormone", *Nature*, Letters to Nature, vol. 375:64–68, (1995).

Mori et al., "Resistance Of AIDS–Associated Kaposi's Sarcoma Cells To Fas–Mediated Apoptosis", *Cancer Research*, vol. 56:1874–1879, (1996).

Cheng et al., "A Bcl–2 Homolog Encoded By Kaposi Sarcoma–Associated Virus, Human Herpesvirus 8, Inhibits Apoptosis But does Not Heterodimerize With Bax Or Bak", *Proc. Natl. Acad. Sci. USA*, The National Academy Of Sciences Of The USA, vol. 94:690–694, (1997).

Cesarman et al., "Kaposi's Sarcoma–Associated Herpesvirus Contains G Protein–Coupled Receptor And Cyclin D Homologs Which Are Expressed In Kaposi's Sarcoma And Malignant Lymphoma", *Journal of Virology*, vol. 70(11):8218–8223, (1996).

Molden et al., "A Kaposi's Sarcoma–Associated herpesvirus–Encoded Cytokine Homolog (vIL–6) Activates Signaling Through The Shared gp130 Receptor Subunit", *The Journal of Biological Chemistry*, The American Society For Biochemistry And Molecular Biology, Inc., vol. 272(31):19625–19631, (1997).

Lee et al., "Kaposi's Sarcoma–Associated Herpesvirus Encodes A Functional Cyclin", *Journal Of Virology*, vol. 71(3):1984–1991, (1997).

Dupon et al., "Acquired Immunodeficiency syndrome–Associated Kaposi's Sarcoma And Human herpesvirus 8 DNA Detection In Serial peripheral Blood Mononuclear Cell Samples", *Res. Virol.*, Institut Pasteur/Elsevier< vol. 148:417–425, (1997).

Tasaka et al., "Is Kaposi's Sarcoma–Associated Herpesvirus Ubiquitous in Urogenital and Prostate Tissues?", Blood; 1997, The American Society of Hematology, Vol 89, No 5: 1686–1689, (1997).

Gao et al., "KSHV antibodies among Americans, Italians, and Ugandans with and without Kaposi's Sarcoma", Nature Medicine, vol. 2, No. 8: 925–927, (Aug. 1996).

Lock et al., "Development of a quantitative polymerase chain reaction for human herpesvirus 8", Journal of Virological Methods 64, Elsevier Science B.V.: 19–26, (1997).

Boshoff et al., "Kaposi's sarcoma–associated herpesvirus infects endothelial and spindle cells", Nature Medicine, vol. 1, No. 12: 1274–1278, (Dec. 1995).

Cathomas et al., "Detection of herpesvirus–like DNA by nested PCR on archival skin biopsy specimens of various forms of Kaposi sarcoma", 2 pages.

Davis et al., "Detection of Serum Antobodies to a Kaposi's Sarcoma–Associated Herpesvirus–Specific Peptide", The Journal of Infectious Diseases, 175: 1071–1979, (1997).

Simpson et al., "Prevalence of Kaposi's sarcoma associated herpesvirus infection measured by antibodies to Recombinant capsid protein and latent immunofluorescence antigen", The Lancet, vol. 348: 1133–1137, (Oct. 26, 1996).

André, et al., "Detection of antobodies against viral capsid proteins of human herpesvirus 8 in AIDS–associated Kaposi's sarcoma", J. Mol. Med 75:145–152, 1997 Springer–Verlag (1997).

Rainbow, Lucille et al., "The 222– to 234–Kilodalton Latent Nuclear Protein (LNA) of Kaposi's Sarcoma–Associated Herpesvirus (Human–Herpesvirus 8) Is Encoded by orf73 and is a component of Latency–Associated Nuclear Antigen", Journal of Virology, American Society of Microbiology, vol. 71, No. 8: 5915–5921, (Aug. 1997).

Kedes, et al., "The seroepidemiology of human herpesvirus 8 (Kaposi's sarcoma–associated herpesvirus): Distribution of infection in KS risk groups and evidence for sexual transmission", Nature Medicine, vol. 2, No. 8:918–924, (Aug. 1996).

Miller et al., "Antibodies to Butyrate–Inducible Antigens of Kaposi's Sarcoma–Associated Herpesvirus in Patients With HIV–1 Infection", The New England Journal of Medicine, vol. 334, No. 20: 1292–1297 (May 16, 1996).

* cited by examiner

SEQUENCE LISTING

<160> NUMBER OF SEQ ID NOS: 11

<210> SEQ ID NO 1
<211> LENGTH: 10
<212> TYPE: PRT
<213> ORGANISM: Human herpesvirus

<400> SEQUENCE: 1

Met Tyr Glu Val Phe Thr Asp Phe Pro Val
 1               5                  10

<210> SEQ ID NO 2
<211> LENGTH: 10
<212> TYPE: PRT
<213> ORGANISM: Human herpesvirus

<400> SEQUENCE: 2

Asp Pro Ala Tyr Thr Asn Asn Thr Glu Ala
 1               5                  10

<210> SEQ ID NO 3
<211> LENGTH: 10
<212> TYPE: PRT
<213> ORGANISM: Human herpesvirus

<400> SEQUENCE: 3

Arg His Met Tyr Lys Pro Ile Ser Pro Gln
 1               5                  10

<210> SEQ ID NO 4
<211> LENGTH: 10
<212> TYPE: PRT
<213> ORGANISM: Human herpesvirus

<400> SEQUENCE: 4

Met Ser Asn Phe Lys Val Arg Asp Pro Val
 1               5                  10

<210> SEQ ID NO 5
<211> LENGTH: 10
<212> TYPE: PRT
<213> ORGANISM: Human herpesvirus

<400> SEQUENCE: 5

Ala Arg Lys Pro Pro Ser Gly Lys Lys Lys
 1               5                  10

<210> SEQ ID NO 6
<211> LENGTH: 10
<212> TYPE: PRT
<213> ORGANISM: Human herpesvirus

<400> SEQUENCE: 6

Gln Glu Glu Gln Glu Leu Glu Glu Val Glu
 1               5                  10

<210> SEQ ID NO 7
<211> LENGTH: 10
<212> TYPE: PRT
<213> ORGANISM: Human herpesvirus

<400> SEQUENCE: 7

Ala Ile Pro Pro Leu Val Cys Leu Leu Ala

-continued

```
<210> SEQ ID NO 8
<211> LENGTH: 12
<212> TYPE: PRT
<213> ORGANISM: Human herpesvirus

<400> SEQUENCE: 8

Pro Thr Tyr Arg Ser His Leu Gly Phe Trp Gln Glu
 1               5                  10

<210> SEQ ID NO 9
<211> LENGTH: 14
<212> TYPE: PRT
<213> ORGANISM: Human immunodeficiency virus

<400> SEQUENCE: 9

Ser Gly Ser Gly Ile Trp Gly Cys Ser Gly Lys Leu Ile Cys
 1               5                  10

<210> SEQ ID NO 10
<211> LENGTH: 14
<212> TYPE: PRT
<213> ORGANISM: Epstein-Barr virus

<400> SEQUENCE: 10

Ser Gly Ser Gly Gln Glu Pro Pro Ala Pro Gln Ala Pro Ile
 1               5                  10

<210> SEQ ID NO 11
<211> LENGTH: 14
<212> TYPE: PRT
<213> ORGANISM: Poliovirus

<400> SEQUENCE: 11

Ser Gly Ser Gly Pro Ala Leu Thr Ala Val Glu Thr Gly Ala
 1               5                  10
```

(POLY)PEPTIDES WHICH REPRESENT THE EPITOPES OF THE HUMAN HERPES VIRUS TYPE 8

The present invention relates to (poly)peptides that are recognized by anti-HHV-8 antibodies of HHV-8 infected patients. By definition, these (poly)peptides shall not comprise naturally occurring HHV-8 proteins. The invention further relates to polymers containing two or more (identical or different) inventory peptides as well as conjugates comprising the inventory peptides and/or polymers thereof. Further we describe mixtures comprising the inventory peptides and/or polymers thereof that are particularly suited for use in procedures to detect anti-HHV-8 antibodies with high sensitivity and specificity. In addition, the present invention relates to a diagnostic kit comprising the inventory peptides, polymers and/or mixtures thereof for the detection of anti-HHV-8 antibodies or diagnosis of HHV-8 infection, respectively.

The human herpesvirus 8 (HHV-8), also known as Kaposi sarcoma associated herpesvirus (KSHV) is the purported etiological agent of Kaposi's sarcoma and certain B cell lymphomas. Kaposi's sarcoma (KS) is the most frequent tumor in AIDS patients, affecting 20–30% of all patients during the course of their HIV infection. In the U.S., the incidence of KS in this risk group is 20,000fold higher than in the general population [1]. In some geographic areas, e.g. in Mediterranean countries or in Africa, the incidence in the general population is significantly higher.

AIDS-associated KS is characterized by an aggressive course and high mortality whereas classical KS is generally relatively indolent and slowly progressing. Other forms of the disease are endemic KS that predominantly affects children and adolescents in Sub-Saharan Africa, and iatrogenic KS in inmnune suppressed transplant recipients.

KS was first described more than a hundred years ago as a relatively rare tumor occurring predominantly in elderly men of Mediterranean or East European origin [2]. The characteristic external manifestations of KS are sharply defined, differently colored (purple, brown, violet or black) nodular lesions of the skin, mostly on the extremities but also in oral mucosa and viscera. Histologically, these lesions consist of long spindle-shaped cells, apparently of endothelial origin, as well as a number of other cell types like fibroblasts, neo-vascular structures, infiltrating leukocytes and extra-vasated red blood cells.

The production of VEGF (vascular endothelial growth factor) is significantly increased in tumor tissue leading to continued angiogenesis and, hence, an extreme vascularization. Already years ago, epidemiological analyses gave hints that an infectious agent might be involved in the development of KS [1, 3]. Using a new PCR technique, Chang and Moore isolated from KS biopsies DNAs from a hitherto unknown human γ-2 herpesvirus [4]. This virus was called KSHV (Kaposi sarcoma associated herpesvirus) or HHV-8 (human herpesvirus 8), respectively. Its 140 kb genome has been recently cloned and sequenced [5].

Since then a series of publications has shown beyond reasonable doubt that all forms of Kaposi's sarcoma are correlated in practically 100% of all cases with the presence of HHV-8 in KS lesions [6–11]. Moreover, PCR detection of HHV-8 is a prognostic marker for later development of Kaposi's sarcoma [12]. Our own work has shown that seroconversion to HHV-8 is detectable on the average already two years before the clinical manifestation of KS.

Most likely HHV-8 is also involved in the pathogenesis of certain lymphoproliferative disorders such as multicentric Castleman's disease (MCD) or primary effusion lymphoma [13, 14]. Some data also hint to a contribution of HHV-8 in interstitial pneumonia and encephalitis [15]. Recently published work suggests that HHV-8 is correlated with multiple myeloma [16]. Although several experimental results are compatible with the hypothesis that HHV-8 may be involved in the pathogenesis of this disease [17–22], a causal relationship is not yet proven. In some geographic regions such as Central Africa, HHV-8 appears to be relatively widespread in the general population [8, 23–25]. Despite a higher incidence of KS in these countries, the presence of an infection with HHV-8 alone appears to be necessary but not sufficient for the development of this disease.

Based on the available viral DNA sequences, several diagnostic tests have been developed that allow a direct or indirect detection of HHV-8. With the help of a relatively simple test, the polymerase chain reaction, even minute quantities of viral DNA can be detected in blood or tissue samples [14, 26–28]. However, for some medical analyses PCR tests are not sensitive enough.

Immunosuppressed organ transplant recipients also have an increased risk of developing Kaposi's sarcoma (up to 5% for kidney transplant recipients); the number of cases varies greatly with geographic origin. In countries of the Near and Middle East, KS is the most common post transplant tumor; worldwide it ranks third. In developed countries (Europe, U.S. or Japan) about 1 to 1.5 m people have an increased risk of getting KS. Blood products for these patients should therefore be unconditionally tested for anti-HHV-8 antibodies as a marker for a possible contamination with HHV-8 in order to keep their infection risk as small as possible. In a broader sense this also applies for other more or less immunocompromised groups, e.g. patients under high dose chemotherapy, dialysis patients, elderly people, neonates etc.

KS predominantly affects people suffering from various forms of immunodeficiency, and is only poorly treatable by chemotherapy, surgery or with ionizing radiation. Presently, there is neither a causative treatment nor a final cure for this disease. One has to consider that immune deficient individuals are exposed to an extraordinary risk to develop Kaposi's sarcoma if they receive HHV-8 contaminated blood products.

For routine diagnostics purposes one mostly uses ELISAs (enzyme-linked immunosorbent assays) because these tests are cheap and suitable for high throughput testing. The detection of HHV-8 specific antibodies indicates prior contact with HHV-8 antigens. This antibody detection can be positive even when the amount of viral DNA (in blood) is below the level of detection in a PCR analysis. Except for ELISAs [29–31], the presence of HHV-8 specific antibodies can also be detected by indirect immunofluorescence assays (IFAs) [25] or Western blots [32, 33].

However, the test procedures that have been described so far are either very time consuming (IFA or Western blot) or not sensitive enough (PCR from blood samples, ELISAs using previously described antigens.

The underlying technical problem for this invention was therefore to define reagents the use of which allows a very sensitive and specific detection of anti-HHV-8 antibodies.

This technical problem is solved by presenting the embodiments detailed in the claims section.

Thus the present invention relates to a (poly)peptide, which is recognized by anti-HHV-8 antibodies in HHV-8 infected patients and is characterized as follows:

(a) it comprises one of the amino acid sequences presented in SEQ ID nos. 1 to 8;

(b) consists of one of the amino acid sequences presented in SEQ ID nos. 1 to 8 or (c) consists of an amino acid sequence which differs from one of the amino acid sequences described in (a) or (b) by one or several substitutions, deletions and/or insertions; wherein the (poly)peptide is not a naturally occurring HHV-8 protein.

Naturally occurring HHV-8 proteins in the sense of this invention are HHV-8 proteins that have the full-length amino acid sequence and are not degraded. Usually or preferentially, the (poly)peptide is recognized by anti-HHV-8 antibodies in bodily fluids of HHV-8 infected individuals. Methods for the determination of the antigenic property of the (poly)peptide related to the invention as well as methods for the isolation of anti-HHV-8 antibodies, preferably from bodily fluids of HHV-8 infected patients are known to those skilled in the art. Such methods comprise for example ELISA tests.

Bodily fluids in the sense of the present invention encompass e.g. blood, serum, plasma, lymph fluid, tissue fluid and extracts, e.g. from mucosa of respiratory, urogenital or gastro-intestinal origin. Further, this expression comprises bodily fluids that have been pretreated to be usable for the above mentioned analysis methods. Examples for this are sera diluted in vitro or treated with preservative agents for cryoprotection (e.g. glycerol) or coagulation inhibition (e.g. heparin).

The term "(poly)peptide" as used in relation to the present invention comprises both peptides and polypeptides. (Poly) peptides related to the invention, which comprise one or more of the amino acid sequences characterized in SEQ ID no. 1 to 8 can be flanked by another HHV-8 sequence as well as by a sequence unrelated to HHV-8. As already mentioned above, said (poly)peptide is not a naturally occurring HHV-8 protein, i.e. said (poly)peptide is not a full length HHV-8 protein as coded by HHV-8 genomes.

Preferably, said (poly)peptides are linear epitopes of different coding regions of the HHV-8 genome, and are less than 50 amino acids in length. More preferred is a length of maximal 15 amino acids, and most preferred is a length of the (poly)peptides related to the invention of 10 to 12 amino acids.

The term "substitution" in the sense of the present invention comprises both conservative and non-conservative exchanges of amino acids. Conservative exchanges are those in which a neutral, hydrophobic, polar, basic or acidic amino acid is replaced by an amino acid of the same class. The different classes of amino acids, the classification of which is determined by specific side chains is well known to those skilled in the art. The crucial point is that the three-dimensional structure of the (poly)peptides is not perturbed in such a way that the peptide is no longer recognized by anti-HHV-8 antibodies.

The peptides related to the invention were identified in a screening of about 3000 peptides according to the following criteria:

(a) minimal homology to peptides of known proteins, in particular to corresponding epitopes of related herpesviruses as for instance EBV and CMV, and (b) maximal antigenicity (by computer prediction)

A preselection of potentially immunodominant HHV-8 specific peptide sequences was achieved by an advantageous combination of different computer programs (BLASTP, ANTIGENIC and BLASTALIGN) of the Genetics Computer Group (GCG), Wisconsin.

All peptides selected by this procedure (292) were then individually tested with a serum pool from KS patients and several control pools from healthy individuals.

The peptides that had passed this initial screen were then analyzed with several hundred sera from KS patients and controls with special attention given to cross-reactions with EBV-, CMV- or HSV-specific antibodies. By these multiple tests, the peptides according to the invention were identified that showed the desired reaction profile.

The (poly)peptides also comprise compounds that are produced by peptidomimetics, preferably (poly)peptides resembling the above mentioned (poly)peptides in their immunological and diagnostic properties. It is known in the art how such molecules can be designed and produced using L- and D-amino acids (e.g. Banerjee, Biopolymers 39 (1996), 769–777). Preferably, the present invention relates to a peptide mix consisting of a combination of said (poly) peptides.

In a preferred embodiment, the peptide mix comprises the (poly)peptides disclosed in SEQ ID nos. 1, 3, 4 and 8.

In an especially preferred embodiment the peptide mix related to the invention contains these (poly)peptides in a molar ratio of 1:1:1:1.

Using the peptide mix according to the invention, anti-HHV-8 antibodies can be detected in an especially advantageous way. Surprisingly, the peptide mix surpasses by far both the sensitivity and the specificity of traditional detection methods (see below).

In another preferred embodiment, the (poly)peptide comprising an amino acid sequence that differs from the amino acid sequences shown in (a) by one or more substitutions, deletions and/or insertions is a naturally occurring sequence variant.

Such peptides that represent sequence variants of the corresponding positions in the genome of HHV-8 (5) may further increase the sensitivity of the detection. The specificity remains unaltered as the selection of peptides by minimal homology to known (viral) proteins excludes highly conserved regions to start with.

In another embodiment, the present invention concerns a polymer comprising at least two identical or different said (poly)peptides.

In the sense of the present invention, such polymers comprise homopolymers consisting of several copies of a single (poly)peptide as well as heteropolymers of any combination of said (poly)peptides whereby such heteropolymers may also contain several copies of one said (poly) peptide.

In a preferred embodiment, the polymer related to the invention is characterized by an unbranched chain of polymerized said (poly)peptides.

In another preferred embodiment, said (poly)peptide is characterized by branched chains of polymerized said (poly) peptides.

Polymers with branched chains of polymerized (poly) peptides are produced by connecting peptides via an amino acid or an amino acid analog that possess two amino groups and one carboxyl group each capable of forming peptide bonds. Such procedures are known in the art.

In another preferred embodiment, the present invention concerns polymers that comprise peptides with the amino acid sequences disclosed in SEQ ID nos. 1, 3, 4 and 8.

In another preferred embodiment, said (poly)peptide is chemically synthesized.

Procedures for chemical synthesis of peptides using peptide synthesizers are known in the art. Preferably, the present invention relates to mixtures consisting of the polymers according to the invention.

In another embodiment, the present invention relates to a fusion protein comprising a (poly)peptide or polymer according to the invention.

In another embodiment, the present invention concerns a polynucleotide coding for a (poly)-peptide, polymer or fusion protein according to the invention.

In a preferred embodiment, the polynucleotide is DNA or RNA.

The present invention further relates to a vector comprising a polynucleotide according to the invention.

In a preferred embodiment, the vector according to the invention is an expression vector.

The term "expression vector" in the sense of the present invention comprises both prokaryotic and eukaryotic expression vectors. The necessary regulatory elements for the expression of a (poly)peptide are known in the art and can be selected to achieve the desired expression. The term "expression" means transcription as well as transcription and translation. In particular, regulatory elements comprise promoters. For expression in prokaryotic cells of a polynucleotide according to the invention a series of suitable promoters exist, e.g. the *E. coli* lac or trp promoter, the lambda phage $P_R$- or $P_L$-promoter lacI, lacZ, T3, T7, gpt etc. Eukaryotic promoters include for instance the CMV immediate early promoter, the HSV promoter, the thymidine kinase promoter, the SV40 promoter, LTRs of retroviruses or the mouse metallothioneinI promoter. A multitude of expression vectors has been described for expression in prokaryotic as well as eukaryotic cells, e.g. for eukaryotes pKK223-3 (Pharmacia Fine Chemicals, Uppsala, Sweden) or GEM1 (Promega Biotech, Madison, Wis., USA), pSV2CAT, pOG44 and for prokaryotes pQE70, pQE60, pBluescript SK, etc. In addition to promoters, vectors according to the invention may also contain other elements that further increase the transcription, e.g. so-called enhancers. Examples are the SV40 enhancer, the polyoma enhancer, the cytomegalovirus early promoter-enhancer and the adenovirus enhancer.

In another embodiment, the present invention relates to a host cell containing an expression vector according to the invention.

The term "host cell" according to the invention comprises prokaryotic as well as eukaryotic host cells. Preferred prokaryotic host cells include e.g. *E. coli* cells, Streptomyces, Bacillus or Salmonella cells, preferred eukaryotic host cells include yeast cells, in particular *Saccharomyces cerevisiae* cells, insect cells as e.g. Drosophila or SF9 cells, animal cells as e.g. CHO or COS cells, plant cells or mammalian cells.

In another embodiment, the present invention relates to a procedure for production of a (poly)peptide, polymer or fusion protein according to the invention comprising the following steps:

(a) cultivation of a host cell according to the invention under conditions that foster the expression of the (poly) peptide, polymer or fusion protein; or (b) in vitro transcription and/or translation of the polynucleotide according to the invention;

and isolation of the (poly)peptide, polymer or fusion protein produced as under (a) or (b).

The conditions for expression of a (poly)peptide are known in the art and can be selected according to the host cell and the expression vector used. The same is true for the isolation of the expression product. When an expression vector is used that leads to the secretion of the synthesized (poly)peptide, the (poly)peptide is isolated from the culture supernatant. When expression takes place intracellularly, the expression product is isolated from the host cell. Methods for in vitro transcription and/or translation are well known in the art. For instance, such procedures may be performed using commercial kits according to the instructions of the manufacturer.

Preferably, additional purification steps known in the art, e.g. column chromatography, may be used for the isolation of said (poly)peptide by removing impurities such as cellular proteins, nucleic acids or components of the in vitro transcription/translation system.

In another embodiment, the present invention relates to a conjugate comprising a (poly)peptide and/or polymer and/or fusion protein according to the invention or a (poly)peptide and/or polymer and/or fusion protein that is produced by said procedure.

In another embodiment, the present invention concerns a composition comprising at least one (poly)peptide and/or polymer and/or fusion protein according to the invention and a conjugate according to the invention, where appropriate also a pharmaceutically compatible carrier and/or diluent.

In a preferred embodiment, the composition is a pharmaceutical.

In an especially preferred embodiment, the pharmaceutical is a vaccine. In this embodiment, the peptides are preferably coupled to a carrier, either individually or in combination. Examples for suitable carriers are polystyrene beads, streptavidin, BSA or KLH.

Examples for suitable pharmaceutically compatible carriers and/or diluents are known in the art and comprise e.g. phosphate buffered sodium chloride solutions, water, emulsions as for instance oilwater emulsions, various forms of surfactants and detergents, sterile solutions etc. Pharmaceuticals comprising such carriers can be formulated according to known conventional methods. These pharmaceuticals may be administered to an individual in a practical dosis, either orally or parenterally (e.g. intravenously, intraperitoneally, subcutaneously, intramuscularly, locally, intranasally, intrabronchially or intradermally or through a catheter into an artery. The physician in charge according to clinical factors determines the dosage and mode of administration. It is known in the art that the dosage depends on various factors such as height, weight, body surface, age, sex or the general health of the patient but also on the characteristics of the administered pharmaceutical, the duration and mode of application as well as on other drugs that may be given simultaneously. A typical dosis may be in a range of 0.001 and 1000 mg whereby dosages below or above this range are conceivable, in particular in consideration of the above mentioned factors. With regular administration of the composition according to the invention, the dosage should generally fall in a range between 1 µg and 10 mg units per day. In case of an intravenous administration (which is not recommended because of the danger of anaphylactic shock), the dosis should be in a range between 1 µg and 10 mg per kg of body weight per minute.

The composition of the invention can be administered locally or systemically. Preparations for a parenteral administration comprise sterile aqueous or non-aqueous solutions, suspensions or emulsions. Examples for non-aqueous solvents are propylenglycol, poly-ethylenglycol, plant oils as e.g. olive oil and organic ester compounds as e.g. ethyloleate that are suitable for injections. Aqueous carriers include water, alcohol-water solutions, emulsions, suspensions, salt solutions and buffered media. Parenteral carriers include sodium chloride solutions, Ringer-dextrose, dextrose and sodium chloride, Ringer-lactate and bonded oils. Intravenous carriers include fluid, nutrient and electrolyte supplements (e.g. those based on Ringer-dextrose). The composition according to the invention may also contain preservatives and other supplements such as antimicrobial compounds, antioxidants, complexing agents and inert gases. Furthermore, depending on the intended use, the composition according to the invention may contain compounds such as interleukins, growth factors, differentiation factors, interferons, chemotactic proteins or unspecifically immunomodulatory agents.

In another embodiment, the present invention relates to a procedure for the detection of anti-HHV-8 antibodies comprising the following steps:

(a) contacting a biological sample with at least one of the (poly)peptides and/or polymer and/or fusion protein according to the invention, a (poly)peptide and/or polymer and/or fusion protein as produced by said method , and/or a conjugate according to the invention, under conditions that allow the binding of antibodies; and (b) detection of the antibodies bound in step (a)

In addition to the detection of anti-HHV-8 antibodies, said procedure is useful as prognostic marker for the eventual development of Kaposi's sarcoma in HIV infected individuals or persons with other natural or iatrogenic immune defects.

In another preferred embodiment, this procedure uses a mixture of (poly)peptides as characterized by the amino acid sequences disclosed in SEQ ID nos. 1, 3, 4 and 8.

The main advantages of said method with respect to previously described procedures [25, 29–34] are on one hand the high sensitivity (>96% of sera from KS patients are positive as opposed to most procedures described in the literature, which only achieve sensitivities between 35 and 85%) and on the other hand a very good specificity and reproducibility (with the ELISA technique duplicate variations are generally less than 5%).

In particular, the use of a combination of different (poly) peptides from different open reading frames of the viral genome rather than individual recombinant antigens such as ORF65 [30] or the Minor Capsid Protein [31] allows the detection of a wider spectrum of HHV-8 specific antibodies. This is especially important with sera from patients who already suffered from a marked immunodeficiency when they were infected with HHV-8 because the antibody titers may be very low in these cases. Other peptide-based immunoassays that use a single peptide achieve a much lower sensitivity [29]. In addition, it is known from other herpesviruses that the use of a single epitope is not sufficient to obtain a diagnostically relevant recognition quota of at least 90% of the true positive sera.

In an especially preferred embodiment of this procedure, said (poly)peptides are chemically synthesized.

By using chemically synthesized peptides rather than recombinant antigens from prokaryotic expression systems or unpurified viral lysates, respectively as employed in other described procedures, a reaction with non-specific antibodies (e.g. against E. coli proteins or against proteins as e.g. EBV or CMV) is practically excluded. In hitherto described procedures, the antigens have to be present at a high degree of purity as even minute amounts of contaminating material (e.g. residual E. coli proteins) can lead to false positive results in many samples. A significant advantage of said procedure is that it does not require such time-consuming and costly purification steps (as e.g. prior adsorption of the test sera to E. coli lysates).

Preferably, the (poly)peptides and/or polymers and/or fusion proteins according to the invention are biotinylated for use in said procedure. The biotinylated components are then bound to a streptavidin-coated solid phase via the highly specific biotin-streptavidin interaction. This coupling procedure ensures an even coating even with mixtures of said (poly)peptides that are different in their charge or their hydrophobicity, respectively.

In another especially preferred embodiment of this procedure, the mixture contains these (poly)peptides in an equimolar ratio.

In another preferred embodiment, said procedure is an enzyme-linked immunosorbent assay (ELISA), an immunodot assay, an immunobead assay, a passive hemagglutination assay (PHA) or a peptide-antibody-peptide sandwich assay.

In another preferred embodiment of said procedure, the biological sample is a pretreated or untreated form of blood, serum, tissue extract, tissue fluid, cell culture supernatant or cell lysate. The term "pretreated form" as used in the sense of the present invention, the reader is redirected to the above definition of the term "bodily fluids" since the possibilities of pretreatment and preparation are also applicable in this context.

In another preferred embodiment, said procedure comprises the additional step:
(c) detection of unspecific binding reactions in step (a) caused by other antibodies that may be present in the biological sample In ELISA tests, additional antibodies may bind independently of the antigen or unspecifically to the surface of the wells of a microplate, thus causing a false positive signal. False positive results due to unspecific binding to the matrix can be safely detected and eliminated by using individual blank wells (without specific antigen). This is of importance for screening of sera in blood banks in order to avoid that donor blood is unnecessarily discarded due to false positive results of HHV-8 tests.

The present invention further relates to a kit, comprising:
(a) at least one (poly)peptide and/or polymer and/or fusion protein according to the invention, a (poly) peptide and/or polymer and/or fusion protein produced according to the invention, and/or a conjugate according to the invention whereby the components may be separated or in form of a mixture; and where appropriate
(b) a solid phase to which at least one (poly)peptide and/or polymer and/or fusion protein according to the invention, a (poly)peptide and/or polymer and/or fusion protein produced according to the invention, and/or a conjugate according to the invention may be bound;
(c) a sample diluent; and/or
(d) a negative control; and/or
(e) a positive control; and/or
(f) a reporter molecule The term "reporter molecule" in the sense of the present invention comprises enzymes as e.g. peroxidase or alkaline phosphatase (in these cases the detection system may be based on a colorimetric reaction as the conversion of ABTS by a peroxidase) as well as other enzymes, radioisotopes, fluorophores, bioluminescent or chemiluminescent molecules and the like or conjugates with e.g. a secondary antibody recognizing e.g. human IgG or IgM antibodies.

Said kit can be used to detect anti-HHV-8 antibodies and to diagnose HHV-8 infections of mammals, preferably in bodily fluids such as blood, serum, tissue extracts, tissue fluids, as well as in in vitro cell culture supernatants and cell lysates (as test reagents). For the intended use, any suitable immunoassay may be chosen, in particular an enzyme-linked immunosorbent assay (ELISA), an immunodot assay, an immunobead assay, a passive hemagglutination assay (PHA), a peptide-antibody-peptide sandwich assay or other methods known in the art.

In a preferred embodiment, the kit contains a mixture of the (poly)peptides consisting of or containing the amino acid sequences disclosed in SEQ ID nos. 1, 3, 4 and 8.

In another embodiment, the present invention relates to the use of at least one (poly)peptide and/or polymer and/or fusion protein according to the invention, a (poly)peptide and/or polymer and/or fusion protein produced according to the invention for the production of a pharmaceutical for treatment of HHV-8 associated diseases.

In a preferred embodiment of the use according to the invention, the HHV-8 associated diseases are Kaposi's sarcoma, multicentric Castleman's disease, primary effusion lymphoma, interstitial pneumonitis, encephalitis and multiple myeloma.

In another embodiment, the present invention concerns the use of at least one (poly)peptide and/or polymer and/or fusion protein according to the invention, a (poly)peptide and/or polymer and/or fusion protein produced according to the invention, and/or conjugate according to the invention for the production of antibodies.

The production of antibodies is well known in the art and comprises e.g. the immunization of an animal with an antigen whereby the antigen may be coupled to a carrier and/or given in combination with other immunostimulating substances (cf. e.g. Harlow and Lane, "Antibodies, a laboratory manual", Cold Spring Harbor Laboratory Press, Cold Spring Harbor, 1988). Other known methods include the screening of antibody libraries with the "phage display" technology and the recombinant production of the desired antibody.

In another embodiment the present invention concerns the use of at least one (poly)peptide and/or polymer and/or fusion protein according to the invention, a (poly)peptide and/or polymer and/or fusion protein produced according to the invention, and/or conjugate according to the invention for the detection of anti-HHV-8 antibodies.

The references cited in the present description are herewith defined to be part of the description.

FIGURE LEGENDS

FIG. 1:

The serum activity against the preferred peptide mix was investigated with HIV-positive/KS-positive and HIV-positive/KS-negative patients. Columns represent the mean reactivity, error bars the standard deviation from the mean reactivity of (i) positive sera, (ii) sera from patients with a CD4 cell count of less than 50/μl, (iii) negative sera. The mean serum reactivity in patients with advanced disease stages is significantly lower than in the total collective.

FIG. 2:

Serum reactivity (CD4 cell count) of an HIV-positive, KS-positive patient were tested using the HHV-8 ELISA (FACS analysis) in a retrospective analysis. HHV-8 specific antibodies are detectable in the blood of this patient already 14 months before the clinical diagnosis of Kaposi's sarcoma. The CD4 cell counts are a measure for the relative immune deficiency of the patient.

FIG. 3:

Schematic representation of the development of the HHV-8 ELISA test

As shown in the following examples, said procedure generally shows positive results years before the clinical diagnosis of Kaposi's sarcoma. Since presently various anti-Herpes drugs are being evaluated as potential KS therapeutics, such substances (or other antiviral substances effective for the treatment of KS) could possibly be used in a preventive way as soon as an infection with HHV-8 is safely diagnosed with the procedure/kit according to the invention.

The following examples illustrate the invention.

EXAMPLE 1

ELISA Test

For the HHV-8 peptide mix ELISA, N-terminally biotinylated peptides of 14 amino acids length are used (10 amino acids of the corresponding antigens plus the tetrapeptide Ser-Gly-Ser-Gly as spacer). The stock solution of the individual peptides (1 μmol/ml in 100% DMSO) was diluted 1:400 in PBS/5% Tween-20 to obtain a working solution used for coating micro-plates pre-coated with streptavidin (Combiplate 8, Life Sciences or MC, MicroCoat). Wells are coated with 100 μl working solution (250 pmol, i.e. a tenfold molar excess over the available amount of bound streptavidin) by incubating for 30 minutes at room temperature. The microplates were then washed twice with PBS/0.2% Tween-20 and were blocked one hour at room temperature with PBS/5% Tween-20. Before incubation with test material (one hour at room temperature with e.g. 1:100 dilutions of human serum), the plates were washed three times with PBS/0.2% Tween-20.

After incubation with the test material, the plates are washed five times and are then incubated for one hour at room temperature with a 1:10,000 dilution of a peroxidase-coupled anti-human IgG or IgM antibody. Thereafter, the plates are again washed five times.

To detect bound conjugate, 200 μl of a 1 mg/ml ABTS solution in peroxidase working solution (Boehringer Mannheim) are added per well, and the plates are incubated 30 minutes at room temperature. The absorption of the wells is measured at 405 nm against a reference wavelength 492 nm. A sample is considered positive when the measured value is higher than 200 mOD above the mean of the control value (without the peptide mix); 200 mOD correspond to at least 4 standard deviations from the mean.

EXAMPLE 2

KS Serum Panel

To verify the serological efficiency, a panel of 380 individual sera from 185 patients with Kaposi's sarcoma was analyzed. Of 256 sera withdrawn after KS diagnosis, 246 were positive with the preferred mixture 1 (peptides no. 1, 3, 4 and 8), which corresponds to a sensitivity of 96.1%. Since this panel includes a good number of sera from HIV patients whose immune system was severely damaged (a condition in which the activation of antibody producing cells is limited), the sensitivity of the test with other panels is presumably even higher.

79 of 96 sera of HIV patients with strongly diminished immune functions (CD4 counts below 50) were positive with the described peptide mix; the mean absorption at a wavelength of 405 nm was 0.342 with a standard deviation of 0.264. For negative sera, the mean absorption was 0.046, and the standard deviation 0.038. 120 sera showed strong immune reaction (O.D.$_{405nm}$>0.6). For these sera, the mean absorption was 1.15±0.49 O.D.$_{405nm}$ (FIG. 1)

EXAMPLE 3

Assay Standardization

To standardize the assay, various plates, blocking methods and diluents were tested. Reproducible coating quality and optimal reaction conditions crucially affect both the sensitivity and the reproducibility of serologic assays. The described. HHV-8. ELISA shows very small intra- and inter-assay variations when the preferred peptide mix is used. The mean coefficient of variation of 79 duplicate determinations of sera with a low reactivity was 4.39%. In patients for whom consecutive sera were available, there was no detectable difference in the results of successive serum samples after the first positive sample. Blank values (incubation of the sera in wells without peptides) are very well reproducible. The mean blank value from 30 plates was 128±45 milliOD

EXAMPLE 4

Control Panels

Various control panels as well as control peptides were used to test the specificity of the HHV-8 antibody ELISA. Using an EBV control peptide (cf. table 2), analyses were carried out to compare antibody titers against HHV-8 and EBV (a closely related herpesvirus). In 56 out of 64 cases the observed antibody titers were at least 30% divergent; the EBV seroprevalence was 86% with HIV-positive patients and 72% with the controls. 28 of 99 sera showed a high reactivity against both HHV-8 and EBV (OD$_{405nm}$>0.6), 39 of 99 sera had high anti-HHV-8 and low anti-EBV titers, 7 out of 99 had low anti-HHV-8 and high anti-EBV titers, and 25 out of 99 sera showed low reactivity against both HHV-8 and EBV antigens (OD$_{405nm}$<0.6). It can be concluded from these data that there was no significant cross-reactivity of the assay with EBV antigens.

EXAMPLE 5

Sensitivity

A highly reactive individual serum was tested in successive twofold dilutions (from 1:50 to 1:12,800). In the calorimetric assay, even the highest dilution yielded an $OD_{405nm}>1.0$. The bandwidth of the assay is limited in this case by the relatively small useable window of the colorimetric detection system. Using more sophisticated detection methods (e.g. chemiluminescence), linear quantitative determinations of the antibody titers should be possible over a range of more than three decades. Thus, one may both quantitate high titered sera and safely recognize low antibody titers.

EXAMPLE 6

Prognostic Value

Figure 2:
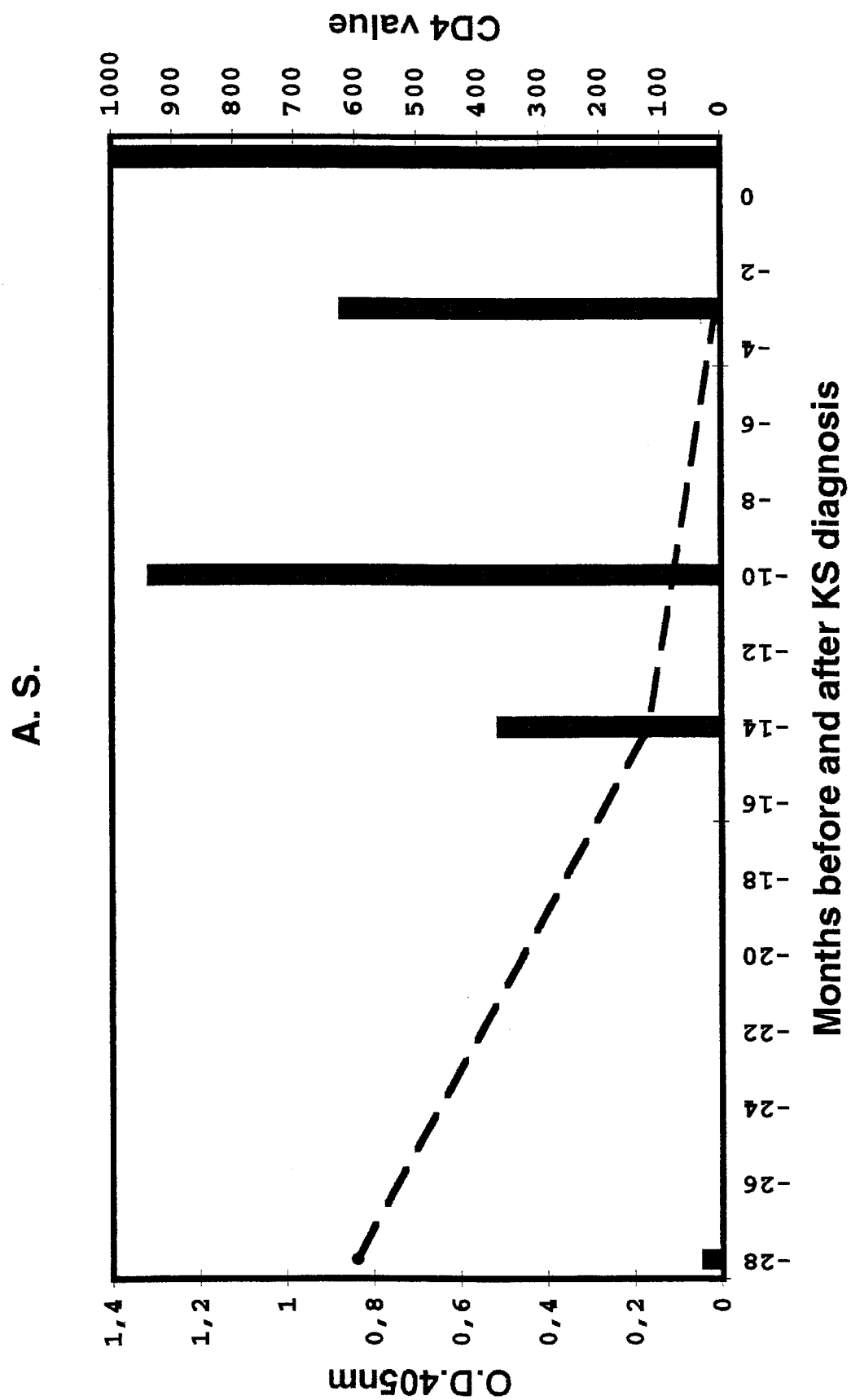
Figure 3:
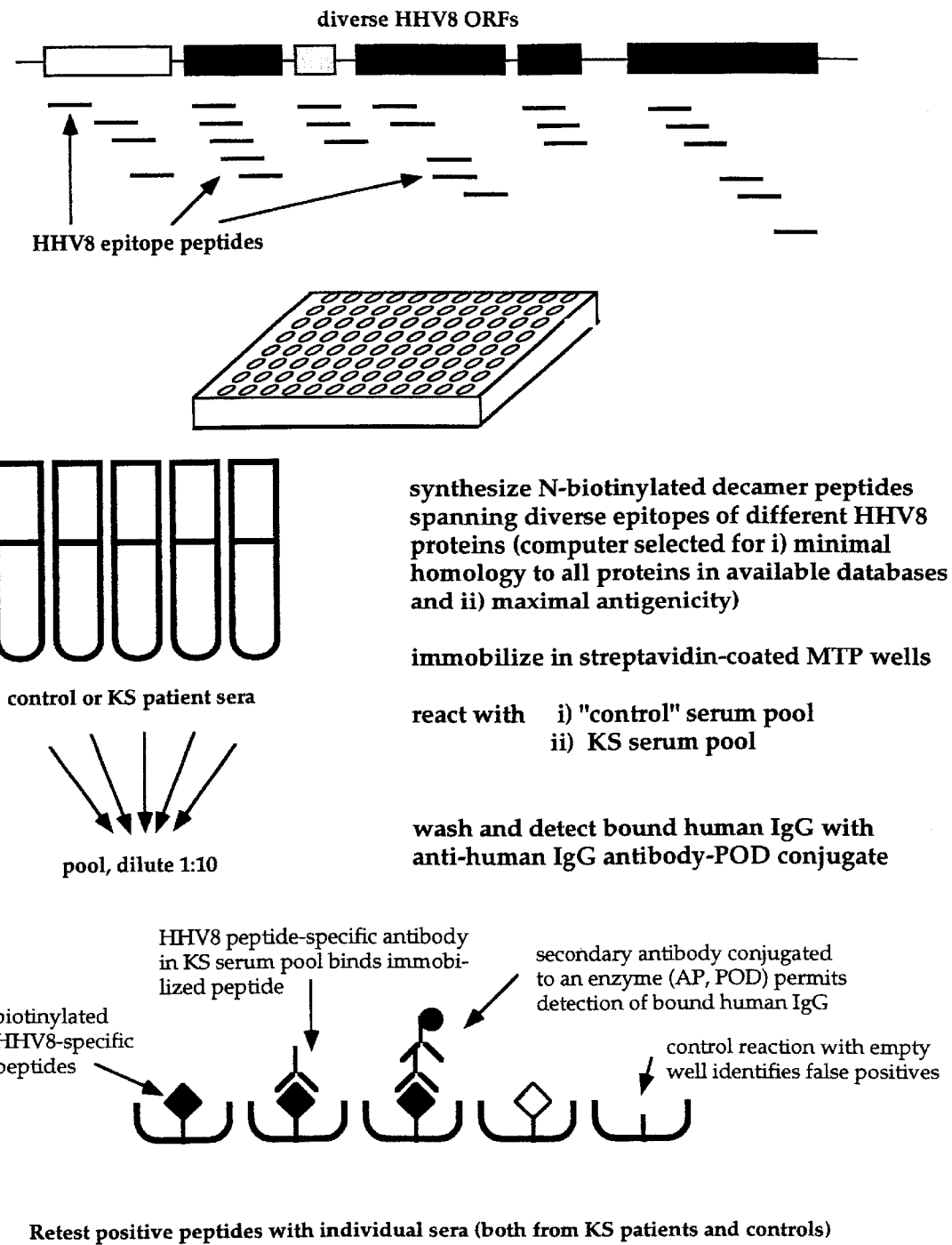

Of 20 KS patients who had been receiving medical treatment over a longer period of time, successive serum samples were analyzed for immune reactivity of HHV-8 specific antibodies. The first positive sample had been withdrawn on the average 20.4±14.6 months prior to the clinical diagnosis. As in most cases the first available serum sample was already tested positive, the real incubation time is probably longer. The ELISA could give hints at an existing risk for the development of a Kaposi's sarcoma. The time course for one of these long-term patients is shown in FIG. 2.

EXAMPLE 7

Exclusion of False Positive Test Results

Of a total of 589 tested KS and control sera, 8 (1.36%) displayed reactivity with the empty wells of the microplates (pre-coated with streptavidin). All these sera were negative in the HHV-8 ELISA after pre-incubation in plates without peptide. Such false positive values can be safely excluded by sample-specific blank values. None of the previously described test systems employs such individual blank values, which is why false positive tests resulting from unspecifically reactive sera cannot be recognized. This additional control prevents the unnecessary exclusion of blood samples and is therefore particularly interesting for blood banks from an economic point of view. As preliminary tests have shown, the proportion of unspecifically reactive sera appears to be much higher in panels from South European and African countries.

EXAMPLE 8

Comparison of Serologic Tests with DNA-based Detection Methods

Of 100 HIV infected test persons, both serum samples and genomic DNA from unfractionated peripheral blood cells were prepared. Sera were analyzed in the HHV-8 peptide mix ELISA, whereas the HHV-8 specific DNA was determined in a polymerase chain reaction (PCR) with a detection limit of 5–10 copies/reaction (=1000–2000 copies/ml blood). In 5% of these cases, the serologic test was positive although the controlled PCR detection remained negative.

References

1. Beral V, Peterman T A, Berkelman R L, Jaffe H W. Kaposi's sarcoma among persons with AIDS: a sexually transmitted infection? Lancet 1990;335:123–8
2. Kaposi M. Idiopathisches multiples Pigmentsarkom der Haut. Arch. Dermatol. Syphil. 1872;4:742–749
3. Archibald C P, Schechter M T, Le T N, Craib K J, Montaner J S, O'Shaughnessy M V. Evidence for a sexually transmitted cofactor for AIDS-related Kaposi's sarcoma in a cohort of homosexual men. Epidemiology 1992;3:203–9
4. Chang Y, Cesarman E, Pessin M S, Lee F, Culpepper J, Knowles D M, Moore P S. Identification of herpesvirus-like DNA sequences in AIDS-associated Kaposi's sarcoma. Science 1994;266:1865–9
5. Russo J J, Bohenzky R A, Chien M C, Chen J, Yan M, Maddalena D, Parry J P, Peruzzi D, Edelman I S, Chang Y, Moore P S. Nucleotide sequence of the Kaposi sarcoma-associated herpesvirus (HHV8). Proc Natl Acad Sci USA 1996;93:14862–7
6. Dupin N, Grandadam M, Calvez V, Gorin I, Aubin J T, Havard S, Lamy F, Leibowitch M, Huraux J M, Escande J P. Herpesvirus-like DNA sequences in patients with Mediterranean Kaposi's sarcoma. Lancet 1995;345:761–2
7. Huang Y Q, Li J J, Kaplan M H, Poiesz B, Katabira E, Zhang W C, Feiner D, Friedman K A. Human herpesvirus-like nucleic acid in various forms of Kaposi's sarcoma. Lancet 1995;345:759–61
8. Luppi M, Barozzi P, Maiorana A, Collina G, Ferrari M G, Marasca R, Morselli M, Rossi E, Ceccherini Nelli L, Torelli G. Frequency and distribution of herpesvirus-like DNA sequences (KSHV) in different stages of classic Kaposi's sarcoma and in normal tissues from an Italian population. Int J Cancer 1996;66:427–31
9. Moore P S, Chang Y. Detection of herpesvirus-like DNA sequences in Kaposi's sarcoma in patients with and without HIV infection. N Engl J Med 1995;332:1181–5
10. Moore P S, Kingsley L A, Holmberg S D, Spira T, Gupta P, Hoover D R, Parry J P, Conley L J, Jaffe H W, Chang Y. Kaposi's sarcoma-associated herpesvirus infection prior to onset of Kaposi's sarcoma. Aids 1996;10:175–80
11. O'Neill E, Henson T H, Ghorbani A J, Land M A, Webber B L, Garcia J V. Herpes virus-like sequences are specifically found in Kaposi sarcoma lesions. J Clin Pathol 1996;49:306–8
12. Whitby D, Howard M R, Tenant-Flowers M, Brink N S, Copas A, Boshoff C, Hatzioannou T, Suggett F E A, Aldam D M, Denton A S, Miller R F, Weller I V D, Weiss R A, Tedder R S, Schulz T F. Detection of Kaposi sarcoma associated herpesvirus in peripheral blood of HIV-infected individuals and progression to Kaposi's sarcoma. Lancet 1995;346:799–802
13. Soulier J, Grollet L, Oksenhendler E, Cacoub P, Cazals H D, Babinet P, d'Agay M F, Clauvel J P, Raphael M, Degos L, et al. Kaposi's sarcoma-associated herpesvirus-like DNA sequences in multicentric Castleman's disease. Blood 1995;86:1276–80
14. Cesarman E, Chang Y, Moore P S, Said J W, Knowles D M. Kaposi's sarcoma-associated herpesvirus-like DNA sequences in AIDS-related body-cavity-based lymphomas. N Engl J Med 1995;332:1186–91
15. Said J W, Tasaka T, de Vos S, Koeffler H P. Kaposi's sarcoma-associated herpesvirus/human herpesvirus type 8 encephalitis in HIV-positive and -negative individuals. Aids 1997; 11: 1119–22
16. Rettig M B, Ma H J, Vescio R A, Pold M, Schiller G, Belson D, Savage A, Nishikubo C, Wu C, Fraser J, Said J W, Berenson J R. Kaposi's sarcoma-associated herpesvirus infection of bone marrow dendritic cells from multiple myeloma patients. Science 1997;276: 1851–4
17. Lunardi-Iskandar Y, Bryant J L, Zeman R A, Lam V H, Samaniego F, Besnier J M, Hermans P, Thierry A R, Gill P, Gallo R C. Tumorigenesis and metastasis of neoplastic Kaposi's sarcoma cell line in immunodeficient mice blocked by a human pregnancy hormone. Nature 1995;375:64–8
18. Mori S, Murakami M K, Jewett A, Nakamura S, Bonavida B. Resistance of AIDS-associated Kaposi's sarcoma cells to Fas-mediated apoptosis. Cancer Res 1996;56: 1874–1879
19. Cheng E H, Nicholas J, Bellows D S, Hayward G S, Guo H G, Reitz M S, Hardwick J M. A Bcl-2 homolog encoded by Kaposi sarcoma-associated virus, human herpesvirus 8, inhibits apoptosis but does not heterodimerize with Bax or Bak. Proc Natl Acad Sci USA 1997;94:690–4
20. Cesarman E, Nador R G, Bai F, Bohenzky R A, Russo J J, Moore P S, Chang Y, Knowles D M. Kaposi's sarcoma-associated herpesvirus contains G protein-coupled receptor and cyclin D homologs which are expressed in Kaposi's sarcoma and malignant lymphoma. J Virol 1996;70:8218–23
21. Molden J, Chang Y, You Y, Moore P S, Goldsmith M A. A Kaposi's sarcoma-associated herpesvirus-encoded cytokine homolog (vIL-6) activates signaling through the shared gp130 receptor subunit. J Biol Chem 1997;272:19625–31
22. Li M, Lee H, Yoon D W, Albrecht J C, Fleckenstein B, Neipel F, Jung J U. Kaposi's sarcoma-associated herpesvirus encodes a functional cyclin. J Virol 1997;71: 1984–91
23. Dupon M, Masquelier B, Cazorla C, Chine G, Dumon B, Ragnaud J M, de Barbeyrac B, Bébéar C, Lacut J Y, Fleury H J. Acquired immunodeficiency syndrome-associated Kaposi's sarcoma and human herpesvirus 8 DNA detection in serial peripheral blood mononuclear cell samples. Res Virol 1997;148:417–25
24. Tasaka T, Said J W, Morosetti R, Park D, Verbeek W, Nagai M, Takahara J, Koeffler H P. Is Kaposi's sarcoma-associated herpesvirus ubiquitous in urogenital and prostate tissues? Blood 1997;89:1686–9
25. Gao S J, Kingsley L, Li M, Zheng W, Parravicini C, Ziegler J, Newton R, Rinaldo C R, Saah A, Phair J, Detels R, Chang Y, Moore P S. KSHV antibodies among Americans, Italians and Ugandans with and without Kaposi's sarcoma. Nat Med 1996;2:925–8
26. Lock M J, Griffiths P D, Emery V C. Development of a quantitative competitive polymerase chain reaction for human herpesvirus 8. J Virol Methods 1997;64: 19–26
27. Boshoff C, Schulz T F, Kennedy M M, Graham A K, Fisher C, Thomas A, McGee J O, Weiss R A, O'Leary J J. Kaposi's sarcoma-associated herpesvirus infects endothelial and spindle cells. Nat Med 1995; 1: 1274–8
28. Cathomas G, McGandy C E, Terracciano L M, Itin P H, De R G, Gudat F. Detection of herpesvirus-like DNA by nested PCR on archival skin biopsy specimens of various forms of Kaposi sarcoma. J Clin Pathol 1996;49:631–3
29. Davis D A, Humphrey R W, Newcomb F M, TR OB, Goedert J J, Straus S E, Yarchoan R. Detection of serum antibodies to a Kaposi's sarcoma-associated herpesvirus-specific peptide. J Infect Dis 1997; 175:1071–9
30. Simpson G R, Schulz T F, Whitby D, Cook P M, Boshoff C, Rainbow L, Howard M R, Gao S J, Bohenzky R A, Simmonds P, Lee C, de Ruiter A, Hatzakis A, Tedder R S, Weller I V, Weiss R A, Moore P S. Prevalence of Kaposi's sarcoma associated herpesvirus infection measured by antibodies to recombinant capsid protein and latent immunofluorescence antigen. Lancet 1996;348:1133–8
31. Andre S, Schatz O, Bogner J R, Zeichhardt H, Stoffler-Meilicke M, Jahn H-U, Ullrich R, Sonntag A-K, Kehm R, Haas J. Detection of antibodies against viral capsid proteins of human herpesvirus 8 in AIDS-associated Kaposi's sarcoma. J. Mol. Med. 1997;75:145–152
32. Rainbow L, Platt G M, Simpson G R, Sarid R, Gao S J, Stoiber H, Herrington C S, Moore P S, Schulz T F. The 222- to 234-kilodalton latent nuclear protein (LNA) of Kaposi's sarcoma-associated herpesvirus (human herpesvirus 8) is encoded by orf73 and is a component of the latency- associated nuclear antigen. J Virol 1997;71:5915–21
33. Kedes D H, Operskalski E, Busch M, Kohn R, Flood J, Ganem D. The sero-epidemiology of human herpesvirus 8 (Kaposi's sarcoma-associated herpesvirus): distribution of infection in KS risk groups and evidence for sexual transmission [published erratum appears in Nat Med 1996 Sep;2(9):1041]. Nat Med 1996;2:918–24
34. Miller G, Rigsby M O, Heston L, Grogan E, Sun R, Metroka C, Levy J A, Gao S J, Chang Y, Moore P. Antibodies to butyrate-inducible antigens of Kaposi's sarcoma-associated herpesvirus in patients with HIV-1 infection. N Engl J Med 1996;334:1292–7

TABLE 1

Peptides found to be reactive with sera from KS patients. Position numbers relate to the published sequence of the HHV-8 genome by Russo et al. (5)(Genbank accession No. U75698)(SEQ ID NOS 1–8, respectively, in order of appearance).

| No. | Seq ID | Position | Sequence | ORF |
|---|---|---|---|---|
| 1 | KS20A | 35573-35544 | M Y E V F T D F P V | tegument |
| 2 | KS29bG | 50000-49971 | D P A Y T N N T E A | packaging protein |
| 3 | KS29bP | 49394-49365 | R H M Y K P I S P Q | packaging protein |
| 4 | KS65A | 112443-112414 | M S N F K V R D P V | capsid |
| 5 | KS65X | 111960-111931 | A R K P P S G K K K | capsid |
| 6 | KS73J | 124726-124697 | Q E E Q E L E E V E | LANA |
| 7 | KSK12D | 118023-117994 | A I P P L V C L L A | kaposin |
| 8 | KS8.1A | 75999-76034 | P T Y R S H L G F W Q E | glycoprotein |

TABLE 2

Sequences of the control peptides used. Position numbers relate to HIV-1 HXB2 (Genbank accession no. M38432), Epstein-Barr virus strain B95-8 (V01555) or poliovirus type Sabin 1 (V01150). The first 4 amino acids in italics (*SGSG*) (portion of SEQ ID NO: 9) in each sequence were introduced as a spacer (SEQ ID NOS 9–11, respectively, in order of appearance).

| No. | Seq ID | Position | Sequence | ORF |
|---|---|---|---|---|
| 1 | HIV B | 8007-8036 | *S G S G* I W G C S G K L I C | TM (gp41) |
| 2 | EBV A | 100695-100724 | *S G S G* Q E P P A P Q A P I | EBNA 6 |
| 3 | polio B | 2603-2632 | *S G S G* P A L T A V E T G A | VP 1 capsid |

What is claimed is:

1. A peptide mixture consisting essentially of a mixture of peptides consisting of the amino acid sequences of SEQ ID Nos.: 5 and 8,
   wherein either peptide is not a full length HHV-8 protein as coded by the HHV-8 genome and the peptide mixture is recognized by anti-HHV-8 antibodies of HHV-8-infected patients.

2. The peptide mixture of claim 1, in which at least one peptide is chemically synthesized.

3. A method for the production of a peptide of the peptide mixture of claim 1 comprising:

(a) culturing a host cell comprising a polynucleotide encoding at least one peptide of claim 1 under conditions that result in the expression of the peptide; or (b) transcribing and translating at least one of said polynucleotides in vitro; and after completion of (a) or (b);

(c) isolating the peptide made by (a) or (b).

4. A composition comprising a peptide mixture of claim 1.

5. The composition of claim 4, which is a pharmaceutical composition.

6. A method for the detection of anti-HHV8 antibodies, comprising:

(a) contacting a biological sample with the peptide mixture of claim 1 under conditions which allow the binding of antibodies to said composition; and (b) detecting the antibodies bound in step (a).

7. The method of claim 6, wherein said method is selected from the group consisting of an enzyme-linked immunoabsorbent assay (ELISA), an enzyme immunodot assay, an immunobead assay, a passive hemagglutination assay (PHA) and a peptide-antibody-peptide sandwich assay.

8. The method of claim 6, wherein the biological sample is selected from the group consisting of blood, serum, tissue extract, tissue fluid, cell culture supernatant and a cell lysate.

9. A kit comprising at least one container comprising individual components or a mixture of components, wherein said components comprise:

(a) the peptide mixture of claim 1, and optionally at least one of the following:

(b) a solid phase, to which at least one of said components may be bound;

(c) a sample diluent;

(d) a negative control;

(e) a positive control; and (f) a reporter molecule.

10. The peptide mixture of claim 1, wherein one or both petides is biotinylated.

* * * * *

UNITED STATES PATENT AND TRADEMARK OFFICE
CERTIFICATE OF CORRECTION

PATENT NO. : 6,669,939 B1
DATED : December 30, 2003
INVENTOR(S) : Octavian Schatz and Jurgen Haas It is certified that error appears in the above-identified patent and that said Letters Patent is hereby corrected as shown below:

Title page,
Item [73], Assignee, please change from "Biotrin International Properties Limited, Mount Merrion (IR)" to -- Biotrin Intellectual Properties Limited, Mount Merrion (IE) --.

Column 18,
Line 65, please change "petides" to -- peptides --.

Signed and Sealed this

Tenth Day of August, 2004

JON W. DUDAS
*Acting Director of the United States Patent and Trademark Office*